(12) United States Patent
Bozzano

(10) Patent No.: US 8,003,841 B2
(45) Date of Patent: Aug. 23, 2011

(54) INTEGRATION OF OTO PROCESS WITH DIRECT DME SYNTHESIS

(75) Inventor: Andrea G. Bozzano, Northbrook, IL (US)

(73) Assignee: UOP LLC, Des Plaines, IL (US)

( * ) Notice: Subject to any disclaimer, the term of this patent is extended or adjusted under 35 U.S.C. 154(b) by 527 days.

(21) Appl. No.: 12/164,946

(22) Filed: Jun. 30, 2008

(65) Prior Publication Data

US 2009/0326298 A1 Dec. 31, 2009

(51) Int. Cl.
C07C 1/02 (2006.01)
B01J 10/00 (2006.01)

(52) U.S. Cl. ........ 585/639; 585/324; 585/326; 585/327; 585/329; 585/634; 585/640; 585/910; 518/718; 422/189

(58) Field of Classification Search ............... 585/324, 585/326, 327, 329, 634, 639, 640, 910; 518/718
See application file for complete search history.

(56) References Cited

U.S. PATENT DOCUMENTS

| | | | |
|---|---|---|---|
| 5,599,955 A | 2/1997 | Vora et al. | |
| 7,151,198 B2 | 12/2006 | Van Egmond | |
| 7,161,051 B2 | 1/2007 | Van Egmond | |
| 2003/0088136 A1* | 5/2003 | Lumgair et al. | 585/640 |
| 2004/0122267 A1 | 6/2004 | Sher et al. | |
| 2006/0020155 A1 | 1/2006 | Beech et al. | |
| 2006/0287405 A1* | 12/2006 | Baek et al. | 518/718 |
| 2007/0155999 A1 | 7/2007 | Pujado et al. | |
| 2007/0203380 A1 | 8/2007 | Vora et al. | |
| 2008/0027150 A1 | 1/2008 | Steynberg | |

FOREIGN PATENT DOCUMENTS

JP 09309851 A 12/1997
KR 10-2005-0028932 A 3/2005

OTHER PUBLICATIONS

PCT International Search Report and Written Opinion for PCT/US2009/043523 dated Jan. 24, 2011.

* cited by examiner

Primary Examiner — Prem C Singh
(74) Attorney, Agent, or Firm — Arthur E Gooding

(57) ABSTRACT

Processes and systems for utilizing products from DME synthesis in converting oxygenates to olefins are provided that include removing a DME-reactor effluent from a DME reactor, wherein the DME effluent includes DME, water, and methanol; separating carbon dioxide gas from the DME reactor effluent in a liquid gas separator to produce a degassed effluent stream. The processes and systems can include feeding the degassed effluent stream to an oxygenate to olefin reactor to produce an olefin containing effluent, wherein the olefin containing effluent further includes oxygenates. Alternatively, the processes and systems can include providing the degassed effluent stream to a DME column to produce a DME feedstock and a solvent stream, wherein the solvent stream includes methanol and water; feeding the DME feedstock to an oxygenate to olefin reactor to produce an olefin containing effluent, wherein the olefin containing effluent further includes oxygenates; and contacting at least a portion of the olefin containing effluent with the solvent stream in a solvent contacting zone to produce an olefin containing raffinate stream and an oxygenate containing extract.

10 Claims, 1 Drawing Sheet

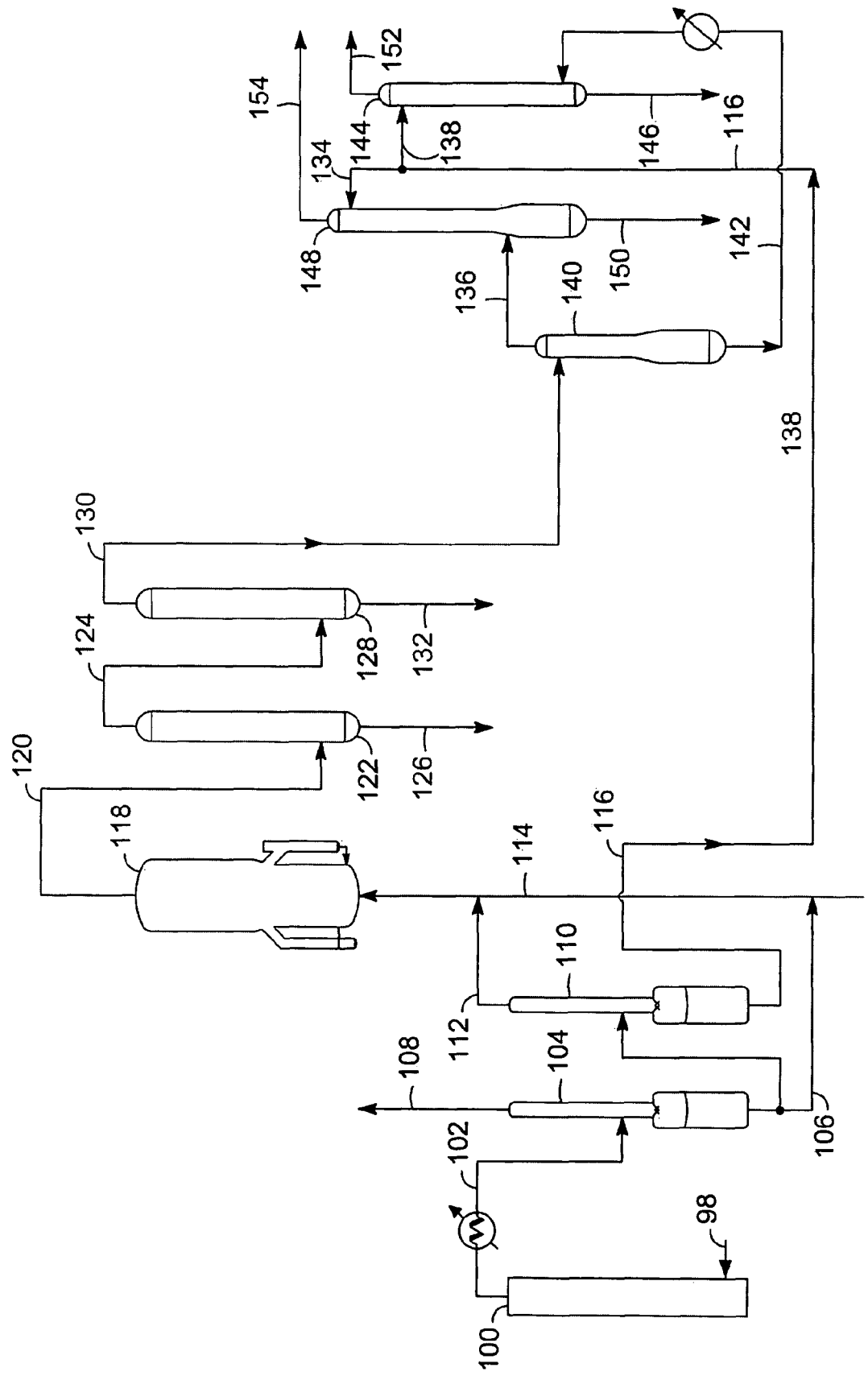

INTEGRATION OF OTO PROCESS WITH DIRECT DME SYNTHESIS

TECHNICAL FIELD

The processes and systems described herein relate to the integration of dimethyl ether (DME) synthesis with oxygenate to olefin (OTO) conversion.

DESCRIPTION OF RELATED ART

Olefins can be produced from hydrocarbon feedstocks, such as petroleum or oxygenates, through various processes, including catalytic conversion or steam cracking processes. Light olefins, such as ethylene and/or propylene, are particularly desirable olefin products because they are useful for making plastics and other chemical compounds. For example, ethylene can be used to make various polyethylene plastics, and in making other chemicals such as vinyl chloride, ethylene oxide, ethylbenzene and alcohol. Propylene can be used to make various polypropylene plastics, and in making other chemicals such as acrylonitrile and propylene oxide.

Oxygenate feedstocks are particularly attractive for use in producing olefins because they are available from a variety of materials, including coal, natural gas, recycled plastics, various carbon waste streams from industry, and various products and by-products from the agricultural industry. DME is one example of an oxygenate feedstock that can be utilized in an oxygenate to olefins process.

DME can be synthesized by several methods. For example, DME can produced by dehydrating methanol into DME and byproduct water in a dehydration unit containing, a methanol dehydration catalyst where the methanol stream is first produced by converting syngas (i.e. a synthesis gas stream containing hydrogen and carbon monoxide) to methanol in a gas phase reactor containing a methanol synthesis catalyst. As another example, the syngas conversion step and methanol dehydration step are combined in a single unit comprising a slurry bubble column reactor (SBCR) containing a bifunctional catalyst system having a methanol synthesis functionality and a methanol dehydration functionality.

SUMMARY

The processes and systems described herein relate to the integration of DME synthesis with oxygenate to olefin conversion. More particularly, the processes and systems described herein relate utilizing products from DME synthesis in converting oxygenates to olefins.

In one aspect, a process for utilizing products from DME synthesis in converting oxygenates to olefins including removing a DME reactor effluent from a DME reactor, wherein the DME effluent includes DME, water, and methanol; separating carbon dioxide gas from the DME reactor effluent in a liquid gas separator to produce a degassed effluent stream; providing the degassed effluent stream to a DME column to produce a DME feedstock and a solvent stream, wherein the solvent stream includes methanol and water; feeding the DME feedstock to an oxygenate to olefin reactor to produce an olefin containing effluent, wherein the olefin containing effluent further includes oxygenates; and contacting at least a portion of the olefin containing effluent with the solvent stream in a solvent contacting zone to produce an olefin containing raffinate stream and an oxygenate containing extract. The process can also include separating the olefin containing effluent to produce a light olefin containing fraction and a heavy olefin containing fraction, wherein the light olefin containing fraction includes ethylene and the heavy olefin containing fraction includes $C_4+$ olefins. In such examples, the portion of the olefin containing effluent in the step of contacting can be the light olefin containing fraction, or the heavy olefin containing fraction. In some examples, at least a portion of the solvent stream can contact the light olefin containing fraction in a first contacting zone, and the heavy olefin containing fraction in a second contact zone.

In another aspect, a process for utilizing products from DME synthesis in converting oxygenates to olefins including: removing a DME reactor effluent from a DME reactor, wherein the DME effluent includes DME, water, and methanol; separating carbon dioxide gas from the DME reactor effluent in a liquid gas separator to produce a degassed effluent stream; and feeding the degassed effluent stream to an oxygenate to olefin reactor to produce an olefin containing effluent, wherein the olefin containing effluent further includes oxygenates.

In a third aspect, a system for utilizing products from DME synthesis in converting oxygenates to olefins that includes: a DME reactor that produces a DME reactor effluent, wherein the DME effluent includes DME, water, and methanol; a liquid gas separator that receives the DME reactor effluent and separates carbon dioxide gas from the DME reactor effluent to produce a degassed effluent stream; a DME column that receives the degassed effluent stream and produces a DME feedstock and a solvent stream, wherein the solvent stream includes methanol and water; an oxygenate to olefin reactor that receives the DME feedstock and produces an olefin containing effluent, wherein the olefin containing effluent further includes oxygenates; and a solvent contacting zone that contacts at least a portion of the olefin containing effluent with the solvent stream to produce an olefin containing overhead stream and an oxygenate containing extract.

BRIEF DESCRIPTION OF THE DRAWINGS

Specific examples have been chosen for purposes of illustration and description, and are shown in the accompanying drawings, forming a part of the specification.

FIG. 1 illustrates a simplified schematic diagram of an integrated DME synthesis and OTO process.

DETAILED DESCRIPTION

FIG. 1 illustrates one example of integrating of DME synthesis with oxygenate to olefin (OTO) conversion. As shown in the FIGURE, DME reactor 100 receives a feed stream 98, and produces a DME reactor effluent 102. The DME effluent includes DME, water, and methanol. The DME reactor effluent 102 can be removed from a DME reactor 100 and passed to a first liquid gas separator 104. The DME reactor effluent 102 can undergo other processing before being passed to the first liquid gas separator 104, such as, for example, undergoing heat exchange in a heat exchanger. The first liquid gas separator 104 can preferably be a carbon dioxide ($CO_2$) column, and that receive the DME reactor effluent 102 and separates carbon dioxide gas from the DME reactor effluent to produce a degassed effluent stream 106 and a carbon dioxide ($CO_2$) stream 108.

The degassed effluent stream 106 includes DME, water and methanol. The degassed effluent stream 106 can be fed to an oxygenate to olefin reactor 118 as all or part of an oxygenate feed stream 114. Alternatively, the degassed effluent stream 106 can be provided to a second liquid gas separator 110. The second liquid gas separator 110 is preferably a DME column that receives the degassed effluent stream 106 and produces a DME feedstock 112 and a solvent stream 116. DME feedstock 112 can be fed to an oxygenate to olefin reactor 118 as all or part of an oxygenate feed stream 114. Preferably, the solvent stream 116 is substantially free of DME, and contains at least a substantial portion of the methanol from the degassed effluent stream 106.

The oxygenate to olefin reactor 118 can receive degassed effluent stream 106 or DME feedstock 112 in oxygenate feed stream 114, and react the oxygenate feed stream 114 with a catalyst under reaction conditions to produce an olefin containing effluent 120. Oxygenate feed stream 114 can be a liquid, a vapor, or a combination thereof. The oxygenate feed stream 114 can be a heated oxygenate feedstock that has undergone heating steps, such as indirect heat exchange with the reactor effluent stream or other process streams, prior to being introduced to the oxygenate to olefin reactor 118. For example, degassed effluent stream 106 or DME feedstock 112 can be heated prior to being fed to the oxygenate to olefin reactor 118, and such, heating can occur in a heat exchanger by indirect heat exchange with the olefin containing effluent.

Oxygenate to olefin reactor 118 can be any catalytic reactor suitable for use in an OTO process, including, for example, fixed bed reactors, fluidized bed reactors, hybrid reactors, and riser reactors. Oxygenate to olefin reactor 118 can include a single zone or multiple zones, and preferably includes a reaction zone containing catalyst and a separation zone. The catalyst contained in oxygenate to olefin reactor 118 can be any catalyst suitable for use in an OTO process, and is preferably a molecular sieve. Molecular sieve catalysts include, for example, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, AFO, AEL, EUO, HEU, FER, MEL, MFI, MTW, MTT, TON, EMT, FAU, ANA, BEA, CFI, CLO, DON, GIS, LTL, MER, MOR, MWW and SOD and substituted forms thereof. Preferred molecular sieve catalysts include zeolites, aluminophosphate (ALPO) molecular sieves, and silicoaluminophosphate (SAPO) molecular sieves, as well as substituted forms thereof.

In oxygenate to olefin reactor 118, the oxygenate feed stream 114 is subjected to reaction conditions suitable for producing the desired level of catalytic conversion and produce olefin containing effluent 120. In some examples, the reaction temperature can be from about 200° C. to about 700° C., preferably from about 250° C. to about 600° C., and more preferably from about 300° C. to about 500° C. The reaction pressure can be any suitable pressure, including autogeneous pressures, and can preferably be from about 0.1 kPa to about 5 MPa, more preferably from about 5 kPa to about 1 MPa, and most preferably from about 20 kPa to about 500 kPa. The term reaction pressure refers to the partial pressure of the feed as it relates to oxygenate compounds and/or mixtures thereof, and does not include the partial pressure of the diluent, if any. The WHSV for the oxygenate conversion reaction, defined as weight of total oxygenate to the reaction zone per hour per weight of molecular sieve in the catalyst in the reaction zone, is another factor that can be varied in the catalytic reactor 102. The total oxygenate to the reaction zone includes all oxygenate in both the vapor and liquid phase. Although the catalyst may contain other materials which act as inerts, fillers or binders, the WHSV is generally calculated using only the weight of molecular sieve in the catalyst in the reaction zone. The WHSV is preferably high enough to maintain the catalyst in a fluidized state under the reaction conditions and within the reactor configuration and design. Preferably, the WHSV can be from about 1 hr$^{-1}$ to about 5000 hr$^{-1}$, more preferably from about 2 hr$^{-1}$ to about 3000 hr$^{-1}$, and most preferably from about 4 hr$^{-1}$ to about 1500 hr$^{-1}$. The oxygenate conversion rate can be any suitable conversion rate, and is preferably maintained sufficiently high to avoid the need for commercially unacceptable levels of feed recycling. Preferably, the oxygenate conversion rates can be from about 50% to about 100%, more preferably from about 95% to about 100%.

Olefin containing effluent 120 can include light olefins, water, and oxygenates. For example, olefin containing effluent 120 can include dimethyl ether, ethylene, propylene, C4 to C6 olefins, and minor amounts of other hydrocarbons and oxygenates. Upon exiting olefin reactor 118, the olefin containing effluent 120 can be a vapor product stream having a relatively high temperature such as, for example, from about 350° C. to about 600° C. (about 660° F. to about 1110° F.). Olefin containing effluent 120 can be removed from oxygenate to olefin reactor 118, and can undergo further processing to separate the olefin containing effluent 120 into various product streams. For example, the olefin containing effluent 120 can be separated, to produce a light olefin containing fraction and a heavy olefin containing fraction, wherein the light olefin containing fraction includes ethylene and the heavy olefin containing fraction includes $C_4$+ olefin.

As illustrated in FIG. 1, the olefin containing effluent 120 can be passed to a quench unit 122. In quench unit 122, water and other unwanted byproducts can be removed from the olefin containing effluent 120 by contacting the olefin containing effluent 120 with a quench medium. The quench medium can be a liquid, and is preferably water. The quench unit produces a vapor product fraction 124 that can include light olefins, dimethyl ether, methane, CO, $CO_2$, ethane, and propane, as well as any water and unreacted oxygenate feed stream that is not condensed in the quench unit 122. The quench unit also produces a liquid product fraction 126 that can contain, water, unreacted oxygenate feedstock, catalyst fines, and oxygenate conversion byproducts such as heavy hydrocarbons, which are generally, defined as being $C_5$ hydrocarbons or greater.

The vapor product fraction 124 can be passed to a product separator 128, which produces a net light olefins stream 130 and a bottoms stream 132. The net light olefins stream 130 can be passed to a light olefins recovery process for further processing and product separation. For example, the net light olefins stream 130 can be passed to a DME stripping zone 140. The net light olefins stream 130 can undergo one or more stages of compression, or other steps, prior to being passed to the DME stripping zone 140. The DME stripping zone separates net light olefins stream 130 to produce a light olefin containing fraction 136 and a heavy olefin containing fraction 142. The light olefin containing fraction 136 includes light olefins such as ethylene, and the heavy olefin containing fraction 142 includes $C_4$+ olefins.

The light olefin containing fraction 136 can be passed to a first solvent contacting zone 148, where it can be contacted with a solvent to remove DME and other oxygenates. Similarly, the heavy olefin containing fraction, 142 can be passed to a second solvent contacting zone 144, where it can be contacted with a solvent.

One suitable solvent source for us in a solvent contacting zone is solvent stream 116. Solvent stream 116, which can recovered from the DME synthesis process as described above, can include methanol and water. Solvent stream 116 can be routed to a unit in the OTO recovery train that is downstream of the oxygenate to olefin reactor 118. For example, solvent stream 116 can be utilized as a solvent in recovering oxygenates from olefin containing effluent 120, or from a separated portion of olefin containing effluent 120, by contacting at least a portion of the olefin containing effluent 120 with at least a portion of the solvent stream 116 in a solvent contacting zone to produce an olefin containing overhead stream and an oxygenate containing extract.

In order to provide an optimal level of solvent performance, water can be added or removed from the solvent stream 116 prior to the solvent stream contacting the olefin containing effluent in the solvent contacting zone. If a solvent stream containing primarily or essentially methanol is desired, then all or substantially all of the water can be removed from solvent stream 116. For example, a liquid gas separator can utilized that removes water from the solvent stream before the solvent stream contacts the olefin containing effluent in the solvent contacting zone.

A solvent contacting zone can be a liquid-liquid extraction zone, a vapor-liquid extraction zone, or an extractive distillation extraction zone. As illustrated in FIG. 1, solvent stream 116, or a first portion thereof 138, can be provided to second solvent, contacting zone 144. Solvent stream 116, or a second portion 134 thereof, can be provided to first solvent contacting zone 148. As discussed above, the heavy olefin containing fraction 142 can be provided to second solvent contacting zone 144. In such an example, the solvent stream 116 can be contacted with the heavy olefin containing fraction 142 in the second solvent contacting zone 144 to produce a first olefin containing raffinate stream 152 and a first oxygenate containing extract 146. In another example discussed above, the light olefin containing fraction 136 can be provided to first solvent contacting zone 148. In such an example, the solvent stream 116 can be contacted with the light olefin containing fraction 136 to produce a second olefin containing raffinate stream 154 and a second oxygenate containing extract 150. Either the first oxygenate containing extract 146, or the second oxygenate containing extract 150, or both, can be routed to the oxygenate to olefin reactor 118.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A process for utilizing products from DME synthesis in converting oxygenates to olefins, the process comprising the steps of:
    removing a DME reactor effluent from a DME reactor, wherein the DME effluent includes DME, water, and methanol;
    separating carbon dioxide gas from the DME reactor effluent in a liquid gas separator to produce a degassed effluent stream;
    providing the degassed effluent stream to a DME column to produce a DME feedstock and a solvent stream, wherein the solvent stream includes methanol and water;
    feeding the DME feedstock to an oxygenate to olefin reactor to produce an olefin containing effluent, wherein the olefin containing effluent further includes oxygenates;
    separating the olefin containing effluent to produce a light olefin containing fraction and a heavy olefin containing fraction, wherein the light olefin containing fraction includes ethylene and the heavy olefin containing fraction includes $C_4+$ olefins;
    contacting the light olefin containing fraction with a first portion of the solvent stream in a first solvent contacting zone to produce a first olefin containing raffinate stream and a first oxygenate containing extract; and
    contacting the heavy olefin containing fraction with a second portion of the solvent stream in a second solvent contacting zone to produce a second olefin containing raffinate stream and a second oxygenate containing extract; and
    routing the second oxygenate containing extract to the oxygenate to olefin reactor.

2. The process of claim 1, wherein the first or second solvent contacting zone is a liquid-liquid extraction zone, a vapor-liquid extraction zone, or an extractive distillation extraction zone.

3. The process of claim 1, wherein the first oxygenate containing extract is routed to the oxygenate to olefin reactor.

4. The process of claim 1, further comprising adding water to the solvent stream prior to the steps of contacting.

5. The process of claim 1, further comprising removing water from the solvent stream prior to the steps of contacting.

6. The process of claim 1, further comprising:
    heating the DME feedstock prior to the step of feeding.

7. The process of claim 6, wherein the step of heating occurs in a heat exchanger by indirect heat exchange with the olefin containing effluent.

8. A process for utilizing products from DME synthesis in converting oxygenates to olefins, the process comprising the steps of:
    removing a DME reactor effluent from a DME reactor, wherein the DME effluent includes DME, water, and methanol;
    separating carbon dioxide gas from the DME reactor effluent in a liquid gas separator to produce a degassed effluent stream; and
    feeding the degassed effluent stream to an oxygenate to olefin reactor to produce an olefin containing effluent, wherein the olefin containing effluent further includes oxygenates;
    separating the olefin containing effluent to produce a light olefin containing fraction and a heavy olefin containing fraction, wherein the light olefin containing fraction includes ethylene and the heavy olefin containing fraction includes $C_4+$ olefins;
    contacting the light olefin containing fraction with a first portion of a solvent stream in a first solvent contacting zone to produce a first olefin containing raffinate stream and a first oxygenate containing extract, the solvent stream including methanol and water; and
    contacting the heavy olefin containing fraction with a second portion of the solvent stream in a second solvent contacting zone to produce a second olefin containing raffinate stream and a second oxygenate containing extract; and
    routing the second oxygenate containing extract to the oxygenate to olefin reactor.

9. The process of claim 8, further comprising:
    heating the degassed effluent stream prior to the step of feeding.

10. The process of claim 9, wherein the step of heating occurs in a heat exchanger by indirect heat exchange with the olefin containing effluent.

* * * * *